United States Patent
Chen (10) Patent No.: US 10,345,458 B2
(45) Date of Patent: Jul. 9, 2019

(54) X-RAY SENSOR AND PIXEL CIRCUIT OF X-RAY SENSOR

(71) Applicant: InnoLux Corporation, Miao-Li County (TW)

(72) Inventor: Yu-Heing Chen, Miao-Li County (TW)

(73) Assignee: INNOLUX CORPORATION, Miao-Li County (TW)

( * ) Notice: Subject to any disclaimer, the term of this patent is extended or adjusted under 35 U.S.C. 154(b) by 0 days.

(21) Appl. No.: 15/886,896

(22) Filed: Feb. 2, 2018

(65) Prior Publication Data

US 2018/0231671 A1 Aug. 16, 2018

(30) Foreign Application Priority Data

Feb. 16, 2017 (CN) .......................... 2017 1 0083763

(51) Int. Cl.
| | |
|---|---|
| *G01T 1/205* | (2006.01) |
| *G01N 23/04* | (2018.01) |
| *G01T 1/208* | (2006.01) |
| *G01T 1/20* | (2006.01) |
| *H01L 27/146* | (2006.01) |

(52) U.S. Cl.
CPC ............ *G01T 1/208* (2013.01); *G01T 1/2018* (2013.01); *H01L 27/14663* (2013.01); *G01N 23/04* (2013.01)

(58) Field of Classification Search
CPC . H01L 27/14663; G01N 23/04; G01T 1/2018; G01T 1/208
See application file for complete search history.

(56) References Cited

U.S. PATENT DOCUMENTS

| | | | | |
|---|---|---|---|---|
| 5,898,753 | A | * | 4/1999 | Schick .................. G01T 1/2018 250/370.09 |
| 2011/0147596 | A1 | * | 6/2011 | Ishida ................ H01L 27/14659 250/366 |
| 2016/0049441 | A1 | * | 2/2016 | Shieh ................ H01L 27/14663 257/43 |

* cited by examiner

*Primary Examiner* — David P Porta
*Assistant Examiner* — Fani Boosalis
(74) *Attorney, Agent, or Firm* — Bacon & Thomas, PLLC (57) ABSTRACT

A pixel circuit of an X-ray sensor includes a photo diode, a first transistor, a second transistor and a third transistor. The photo diode is used to sense X-rays and to generate a corresponding electrical sensing signal. The first transistor is electrically connected with the photo diode to reset the electrical sensing signal. The second transistor is electrically connected with the photo diode to amplify the electrical sensing signal and to generate an amplified sensing signal. The third transistor is electrically connected with the second transistor to output the amplified sensing signal. The second transistor has a terminal electrically connected with a high voltage, and the first transistor has a terminal electrically connected with a calibration voltage. The high voltage and the calibration voltage are controlled separately.

20 Claims, 10 Drawing Sheets

X-RAY SENSOR AND PIXEL CIRCUIT OF X-RAY SENSOR

BACKGROUND

1. Field of the Disclosure

The present disclosure relates to the technical field of X-ray detection and, more particularly, to an X-ray sensor and a pixel circuit of the X-ray sensor.

2. Description of Related Art

X-ray sensors are generally categorized into passive pixel sensors (PPSs) and active pixel sensors (APSs).

A passive pixel sensor (PPS) has a simple structure, in which each sensing pixel is composed only of a transistor and a photo diode. The X-ray becomes a visible light through a scintillator, and the photons of the visible light are converted to the charges through the photo diode, being stored in the sensing pixels. By turning on/off the transistor, the corresponding charges can be read out again.

In an active pixel sensor (APS), each sensing pixel has an amplifying transistor. The amplifying transistor is used to amplify the charges generated by the photo diode. Hence, in the design of the active pixel sensor (APS), the intensity of the sensing signal corresponding to the X-ray is determined not only by the photo diode, but also by the amplifying transistor. Hence, in the active pixel sensor (APS), the sensing signal corresponding to the X-ray is affected by the characteristic of the amplifying transistor, for example, the phenomenon of the threshold voltage shift (Vth shift). Moreover, because of the manufacturing variation, the photo diode of each pixel circuit of the X-ray sensor may have different capacitance. Hence, even if being exposed to the same X-ray, they may generate different voltages, resulting in non-uniformity for the whole image. In view of the above, the pixel circuit of the prior art X-ray sensor is desired to be improved.

SUMMARY

The present disclosure aims to provide a pixel circuit of the X-ray sensor, which can dynamically compensate for the threshold voltage shift of transistors and the capacitance variation of photo diodes, thereby improving the accuracy of imaging provided by the pixel circuits of the X-ray sensor.

In one aspect of the present disclosure, there is provided a pixel circuit of the X-ray sensor, which comprises a photo diode, a first transistor, a second transistor and a third transistor. The photo diode is used to sense X-rays and to generate a corresponding electrical sensing signal. The first transistor is electrically connected with the photo diode to reset the electrical sensing signal. The second transistor is electrically connected with the photo diode and the first transistor to amplify the electrical sensing signal and to generate an amplified sensing signal. The third transistor is electrically connected with the second transistor, to output the amplified sensing signal, wherein the second transistor has a terminal electrically connected with a high voltage, the first transistor has a terminal electrically connected with a calibration voltage, and the high voltage and the calibration voltage are controlled separately.

In another aspect of the present disclosure, there is provided an X-ray sensor, which comprises a carrier, a substrate, a plurality of pixel circuits, a scintillator layer and a protective layer. The substrate is disposed on the carrier. The pixel circuits are disposed on the substrate. Each pixel circuit includes a photo diode, a first transistor, a second transistor and a third transistor. The photo diode is used to sense X-rays and to generate a corresponding electrical sensing signal. The first transistor is electrically connected with the photo diode to reset the electrical sensing signal, wherein the first transistor has a terminal electrically connected with a calibration voltage. The second transistor is electrically connected with the photo diode and the first transistor to amplify the electrical sensing signal, and to generate an amplified sensing signal, wherein the second transistor has a terminal electrically connected with a high voltage. The high voltage and the calibration voltage are controlled separately. The third transistor is electrically connected with the second transistor to output the amplified sensing signal. The scintillator layer is disposed on the pixel circuits to convert the X-ray into a visible light, allowing the photo diode to generate the corresponding electrical sensing signal. The protective layer is disposed on the scintillator layer.

Other objects, advantages, and novel features of the disclosure become more apparent from the following detailed description when taken in conjunction with the accompanying drawings.

DETAILED DESCRIPTION OF THE PREFERRED EMBODIMENT

Figure 1:
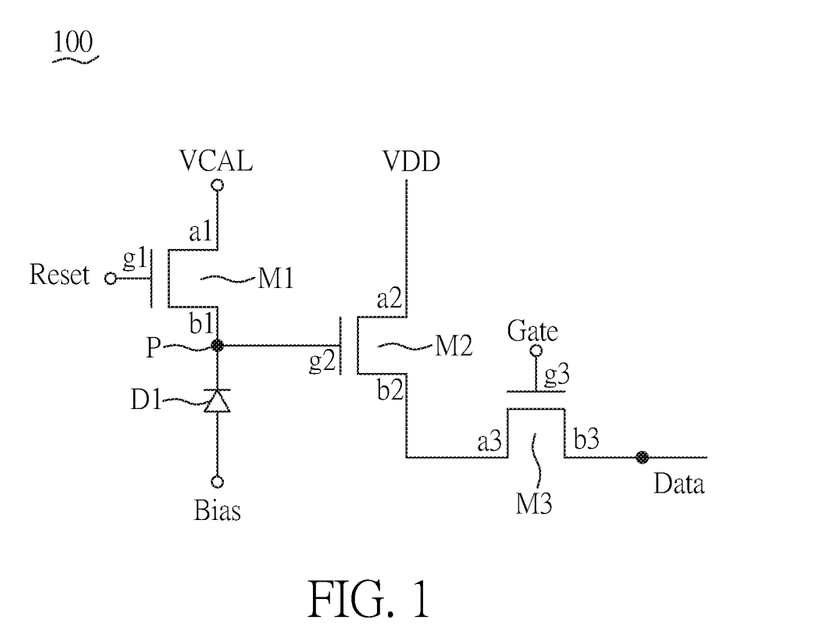
FIG. 1 is a circuit diagram of the pixel circuit of an X-ray sensor according to the present disclosure.

FIG. 1 is a circuit diagram of the pixel circuit 100 of an X-ray sensor according to the present disclosure. In this embodiment, each pixel of the X-ray sensor is corresponding to a pixel circuit 100. The pixel circuit 100 includes a photo diode D1, a first transistor M1, a second transistor M2 and a third transistor M3. The photo diode D1 is used to sense X-rays and to generate a corresponding electrical sensing signal. The electrical sensing signal can be produced by charge, current or voltage. The first transistor M1 is electrically connected with the photo diode D1 to reset the electrical sensing signal. The second transistor M2 is electrically connected with the photo diode D1 and the first transistor M1 through a node P to amplify the electrical sensing signal and to generate an amplified sensing signal. The third transistor M3 is electrically connected with the second transistor M2 to output the amplified sensing signal, wherein the second transistor M2 has a terminal electrically connected with a high voltage VDD, and the first transistor M1 has a terminal electrically connected with a calibration voltage VCAL. The calibration voltage VCAL is variable. The high voltage VDD may be different from the calibration voltage VCAL. In other words, in this embodiment, the high voltage VDD and the calibration voltage VCAL are electrically connected with the second transistor M2 and the first transistor M1 through different wires, respectively. Since the high voltage VDD and the calibration voltage VCAL are respectively connected with different wires, the high voltage VDD and the calibration voltage VCAL can be controlled separately, and thus the high voltage VDD can be the same as or different from the calibration voltage VCAL. The electrical connection in the present disclosure can be a direct electrical connection between two components, a direct electrical connection between two components through wires or semiconductor layers, or a connection between two components through other components (such as capacitors or transistors).

Figure 6:
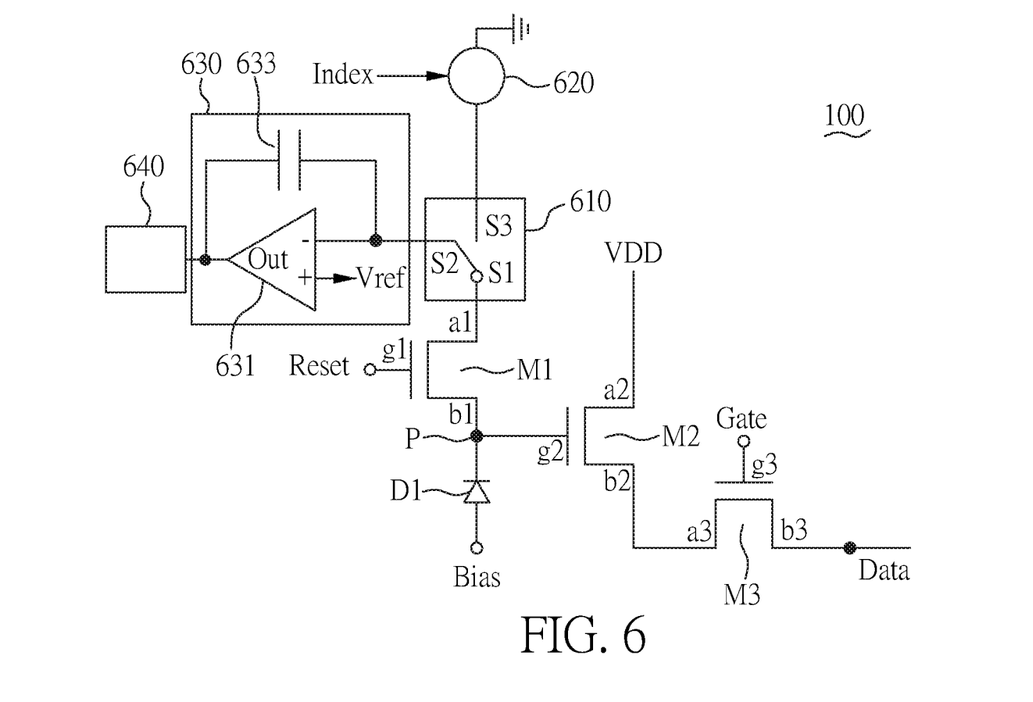
FIG. 6 is a circuit diagram of an embodiment of the pixel circuit of an X-ray sensor according to the present disclosure.

As shown in FIG. 1, the first transistor M1 has a control terminal g1 electrically connected with a first control signal Reset, a first terminal a1 electrically connected with calibration voltage VCAL, and a second terminal b1 electrically connected with a terminal of the photo diode D1. The second transistor M2 has a control terminal g2 electrically connected with the photo diode D1, a first terminal a2 electrically connected with the high voltage VDD, and a second terminal b2. The third transistor M3 has a control terminal g3 electrically connected with a second control signal Gate, a first terminal a3 electrically connected with the second terminal b2 of the second transistor M2, and a second terminal b3. The second terminal b3 of the third transistor M3 can be electrically connected with a readout circuit (not shown, but it can be referred, for example, to the readout circuit 630 as shown in FIG. 6) through a node Data to read out the amplified sensing signal. The other terminal of the photo diode D1 can be electrically connected with a bias signal Bias.

Figure 2:
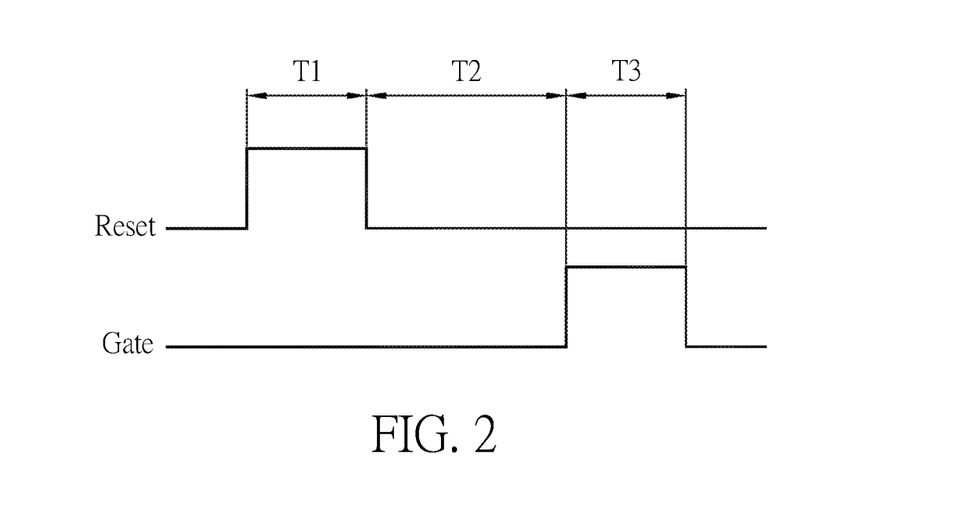
FIG. 2 is a timing diagram of the pixel circuit of an X-ray sensor according to the present disclosure.

FIG. 2 is a timing diagram of the pixel circuit 100 of an X-ray sensor according to the present disclosure. As shown, in a first time period T1, the first control signal Reset is a first high voltage, and, at this moment, the first transistor M1 is turned on to reset the voltage of the node P to the calibration voltage VCAL. In a second time period T2, the first control signal Reset is a low voltage, and, at this moment, the first transistor M1 is turned off, and the photo diode D1 is exposed to the X-ray and thus generates a corresponding electrical sensing signal. The electrical sensing signal decreases the voltage of the node P. Even if the voltage of the node P is decreased, it is still capable of turning on the second transistor M2, because the decreasing range of the voltage of the node P is limited by design. Because of the voltage (electrical sensing signal) change of the node P, a voltage difference occurs between the control terminal g2 and the second terminal b2 of the second transistor M2, and thus a current ID (the amplified sensing signal) is induced from the high voltage VDD through second transistor M2. In a third time period T3, the second control signal Gate is a second high voltage, and the third transistor M3 is turned on, and thus the readout circuit can read out the amplified sensing signal (the current ID), wherein the first high voltage can be the same as or different from the second high voltage. Since the high voltage VDD and the calibration voltage VCAL are respectively connected with different wires, the high voltage VDD and the calibration voltage VCAL can be controlled separately, and thus the high voltage VDD can be the same as or different from the calibration voltage VCAL.

Figure 3:
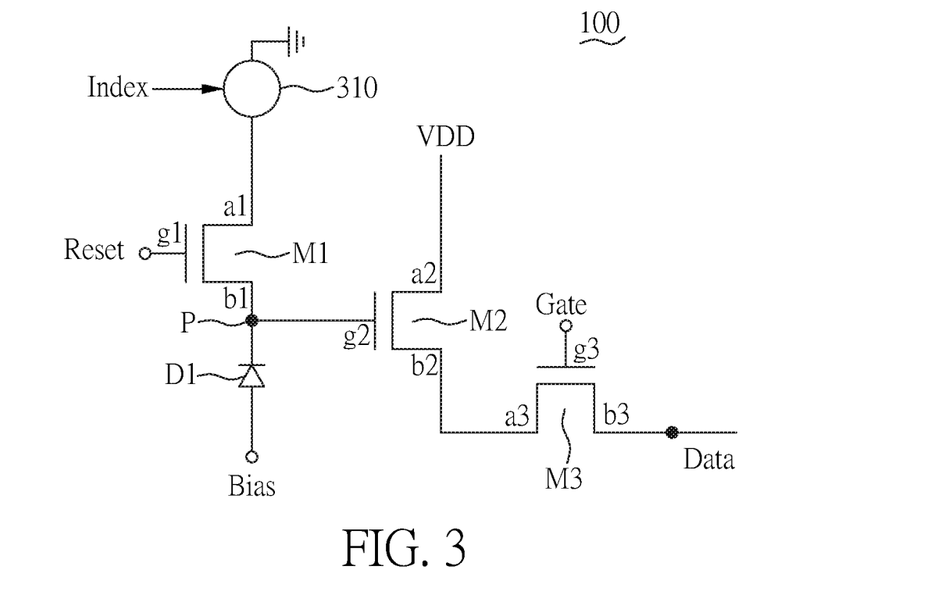
FIG. 3 is a circuit diagram of an embodiment of the pixel circuit of an X-ray sensor according to the present disclosure.

FIG. 3 is a circuit diagram of an embodiment of the pixel circuit 100 of an X-ray sensor according to the present disclosure, which is similar to FIG. 1 except that the pixel circuit 100 in FIG. 3 further includes a programmable voltage source 310. The programmable voltage source 310 is electrically connected with the first terminal a1 of the first transistor M1 to the calibration voltage VCAL to the first transistor M1. The programmable voltage source 310 may generate a different calibration voltage VCAL according to an indication signal Index.

Since the first transistor M1 and the third transistor M3 are used as switches, and the second transistor M2 is used as an amplifier, the current ID (the amplified sensing signal) is affected by the threshold voltage shift (Vth shift) of the second transistor M2, and this decreases the detection accuracy of the pixel circuit 100. Moreover, different photo diodes D1 of different pixels may have different capacitances caused by the manufacture variation. When different pixels are exposed to the same X-ray, different photo diodes D1 generate different corresponding electrical sensing signals, and this decreases the detection accuracy of the pixel circuit 100. By using different calibration voltages VCAL1, VCAL2, . . . , VCALN generated by the programmable voltage source 310, the second transistor M2 can generate different amplified sensing signals (currents ID1, ID2, . . . , IDN) according to the different calibration voltage VCAL1, VCAL2, . . . , VCALN, respectively. The third transistor M3 can output the amplified sensing signals (the currents ID1, ID2, . . . , IDN) to the readout circuit to obtain different calibration voltages and the corresponding amplified sensing signals. With the different calibration voltage and the corresponding amplified sensing signal, it is possible to obtain a bias of the pixel circuit 100, for example, the threshold voltage shift (Vth shift) of the second transistor M2. With the bias of the pixel circuit 100, it is possible to perform compensation to the pixel circuit 100 by software, so as to reduce the influence on the current ID (the amplified sensing signal), induced by the bias of the pixel circuit 100.

In other cases, when the first transistor. M1 is turned off, it is possible to apply different calibration voltages VCAL1, VCAL2, . . . , VCALN to the photo diode D1 through the bias signal terminal, thereby allowing the photo diode D1 to generate different electrical sensing signals. In this way; it is also possible to use the aforementioned steps to obtain the bias of the pixel circuit 100, so as to measure and compensate the pixel circuit 100, wherein the electrical sensing signal can be of charge, current or voltage.

Figure 4:
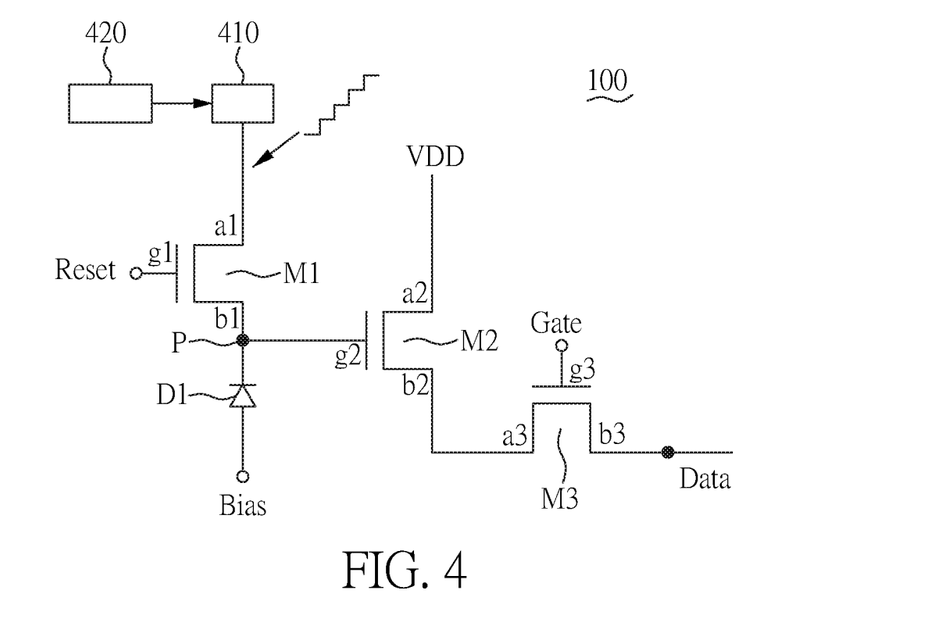
FIG. 4 is a circuit diagram of an embodiment of the pixel circuit of an X-ray sensor according to the present disclosure.

FIG. 4 is a circuit diagram of an embodiment of the pixel circuit 100 of an X-ray sensor according to the present disclosure, which is similar to FIG. 1 except that the pixel circuit 100 in FIG. 4 further includes a digital-to-analog converting circuit 410 and a control unit 420. The digital-to-analog converting circuit 410 is electrically connected with the first terminal al of the first transistor M1 to provide a calibration voltage VCAL, The control unit 420 is electrically connected with the digital-to-analog converting circuit 410 to control the digital-to-analog converting circuit 410 to generate the calibration voltage VCAL. For the circuit in FIG. 4, the aforementioned steps can be used to obtain the bias of the pixel circuit 100, for example, the threshold voltage shift (Vth shift) of the second transistor M2, so as to make compensation to the pixel circuit 100. This can be achieved by a person skilled in this art based on the present disclosure, and thus a detailed description therefor is deemed unnecessary.

Figure 5:
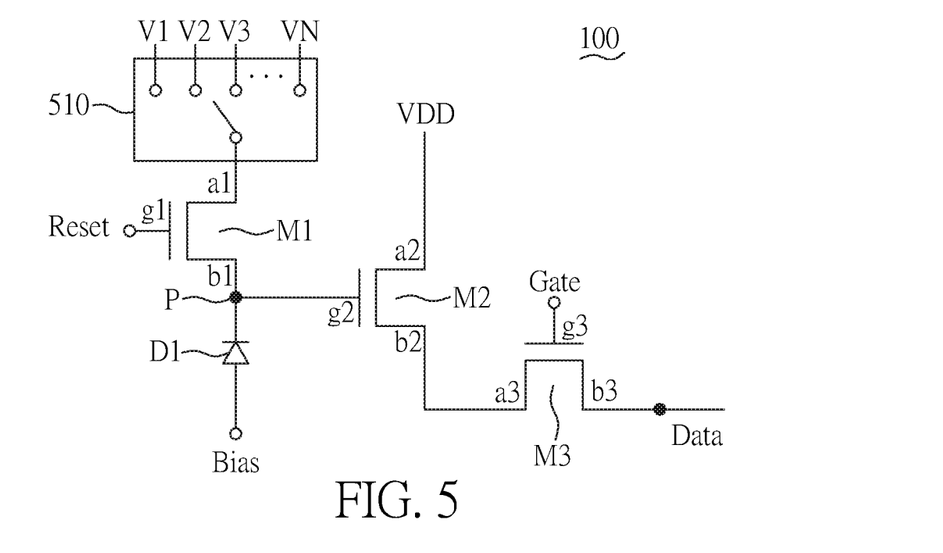
FIG. 5 is a circuit diagram of an embodiment of the pixel circuit of an X-ray sensor according to the present disclosure.

FIG. 5 is a circuit diagram of an embodiment of the pixel circuit 100 of an X-ray sensor according to the present disclosure, which is similar to FIG. 1 except that the pixel circuit 100 in FIG. 5 further includes an N-to-1 switch 510. The N-to-1 switch 510 is electrically connected with the first terminal al of the first transistor M1, wherein the N-to-1 switch 510 has N input terminals electrically connected with N different voltages V1, V2, . . . , VN each serving as a different calibration voltage VCAL, and the N-to-1 switch 510 has an output terminal electrically connected with the first terminal al of the first transistor M1 to provide the calibration voltage VCAL to the first transistor M1, where N is a positive integer greater than 1. For the circuit in FIG. 5, the aforementioned steps can also be used to obtain the bias of the pixel circuit 100, for example, the threshold voltage shift (Vth shift) of the second transistor M2, so as to make compensation to the pixel circuit 100.

FIG. 6 is a circuit diagram of an embodiment of the pixel circuit 100 of an X-ray sensor according to the present disclosure, which is similar to FIG. 1 except that the pixel circuit 100 in FIG. 6 further includes a switch 610, a programmable voltage source 620, a readout circuit 630 and an analog-to-digital converting circuit 640.

The switch 610 is electrically connected with the first transistor M1. The switch 610 has a first terminal S1 electrically connected with the first terminal al of the first transistor M1, a second terminal S2 electrically connected with the readout circuit 630, and a third terminal S3 electrically connected with the programmable voltage source 620, wherein the switch 610 can be switched to allow the first terminal S1 to be electrically connected with the second terminal S2, or the first terminal S1 to be electrically connected with the third terminal S3.

The programmable voltage source 620 can be electrically connected with the switch 610 to provide the calibration voltage VCAL. The programmable voltage source 620 can generate a different calibration voltage VCAL according to an indication signal Index.

The readout circuit 630 can be electrically connected with the switch 610 to perform an integral operation on the electrical sensing signal. The readout circuit 630 includes an operational amplifier 631 and a capacitor 633. The operational amplifier 631 has an inverting terminal (−) electrically connected with the first terminal S1 of the switch 610, and a non-inverting terminal (+) electrically connected with a reference voltage Vref. The capacitor 633 has one terminal electrically connected with the inverting terminal (−), and another terminal electrically connected with an output terminal Out of the operational amplifier 631. The analog-to-digital converting circuit 640 is electrically connected with the output terminal. Out of the operational amplifier 631.

When the switch 610 is switched to allow the first transistor M1 to be electrically connected with the programmable voltage source 620, the calibration voltage VCAL can be outputted to the node P among the first transistor M1, the second transistor M2 and the photo diode D1 through the programmable voltage source 620. That is, when first terminal S1 of the switch 610 is electrically connected with the third terminal S3 thereof, the programmable voltage source 620 can provide the calibration voltage VCAL to the node P.

When the switch 610 is switched to allow the first transistor M1 to be electrically connected with the readout circuit 630, the voltage of the node P can be outputted to the readout circuit 630 through the first transistor M1, then being converted to a corresponding digital signal by the analog-to-digital converting circuit 640. That is, when the first terminal S1 of the switch 610 is electrically connected with the second terminal S2 thereof; the analog-to-digital converting circuit 640 obtains the voltage of the node P. The voltage of the node P represents the capacitance variation of the photo diode D1 caused by the manufacturing process. By writing the voltages into the node P and measuring the voltage of the node P for several times, the capacitance variation of the photo diode D1 can be obtained, so as to perform compensation to the capacitance variation of the photo diode D1.

Figure 7:
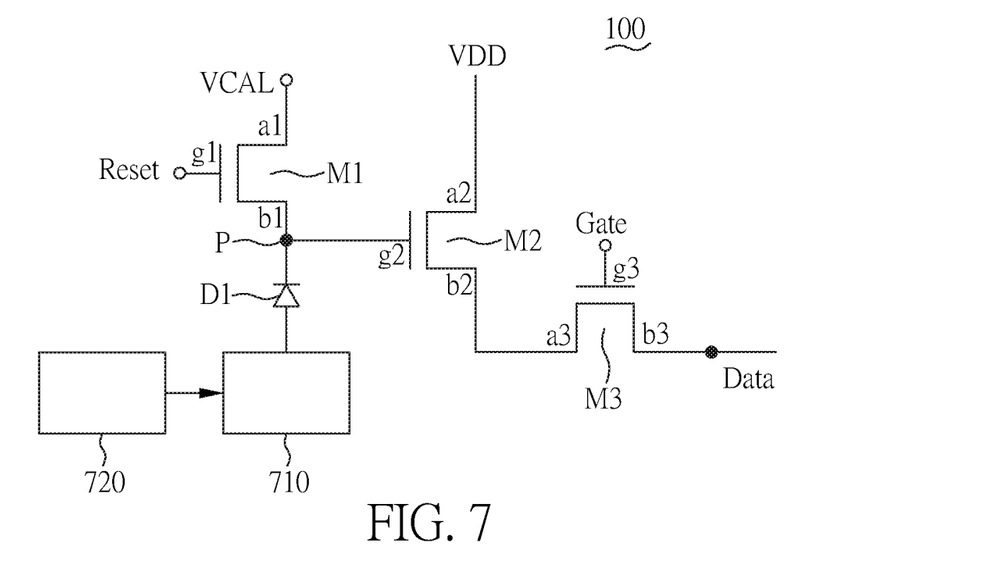
FIG. 7 is a circuit diagram of an embodiment of the pixel circuit of an X-ray sensor according to the present disclosure.

FIG. 7 is a circuit diagram of an embodiment of the pixel circuit 100 of an X-ray sensor according to the present disclosure, which is similar to FIG. 1 except that the pixel circuit 100 in FIG. 7 further includes a digital-to-analog converting circuit 710 and a control unit 720. The digital-to-analog converting circuit 710 can be electrically connected with the photo diode D1. The control unit 720 can be electrically connected with the digital-to-analog converting circuit 710 to control the digital-to-analog converting circuit 710 to generate a photo diode calibration voltage. When first transistor M1 is turned off, the digital-to-analog converting circuit 710 outputs a different voltage to the photo diode D1, and the second transistor M2 generates different amplified sensing signals (the currents ID1, ID2, . . . , IDN). The readout circuit can obtain the amplified sensing signal (the currents ID1, ID2, . . . , IDN) through the third transistor M3, and further obtain the bias of the pixel circuit 100. In other embodiments, with circuits similar to FIG. 7, it is possible to apply the different calibration voltages VCAL1, VCAL2, . . . , VCALN generated by the programmable voltage source 310 in FIG. 3 to the bias signal terminal of the photo diode D1. In other embodiments, the output terminal of the N-to-1 switch 510 in FIGS is electrically connected with the bias signal terminal of the photo diode D1 to provide different calibration voltages VCAL1, VCAL2, . . . , VCALN to the bias signal terminal of the photo diode D1. With the different amplified sensing signals, the bias of the pixel circuit 100 can be Obtained. With the bias of the pixel circuit 100, it is possible to perform compensation to the pixel circuit 100, so as to reduce the influence on the current ID (the amplified sensing signal), induced by the bias of the pixel circuit 100.

Figure 8:
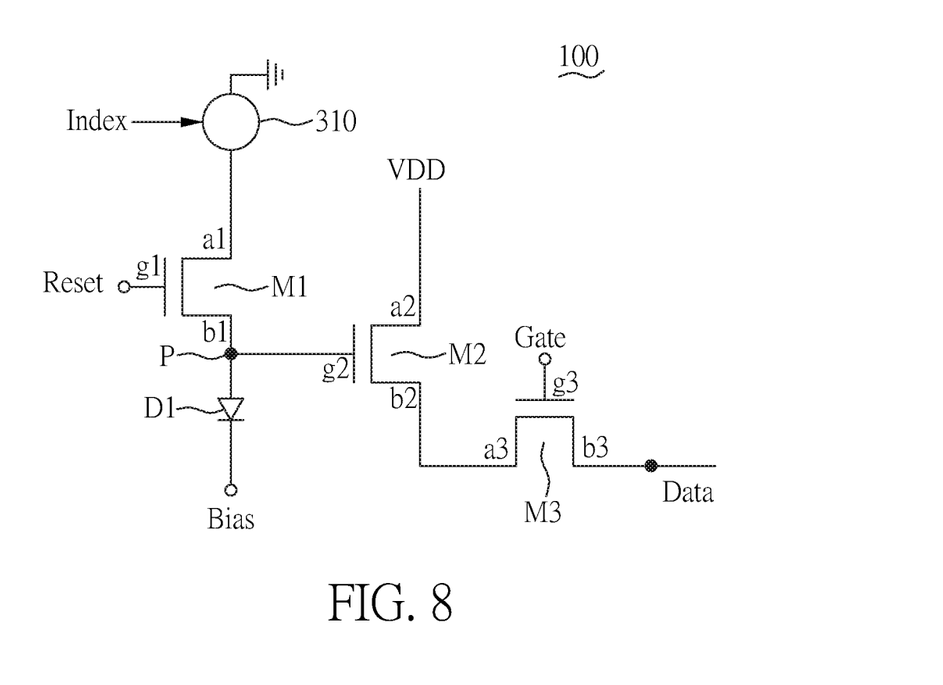
FIG. 8 is a circuit diagram of an embodiment of the pixel circuit of an X-ray sensor according to the present disclosure.

FIG. 8 is a circuit diagram of an embodiment of the pixel circuit 100 of an X-ray sensor according to the present disclosure, which is similar to FIG. 3 except that the photo diode D1 in FIG. 8 is a positive-intrinsic-negative (P-intrinsic-N, PIN) photo diode, while the photo diode D1 in FIG. 3 is a negative-intrinsic-positive (N-intrinsic-P, NIP) photo diode.

Figure 9:
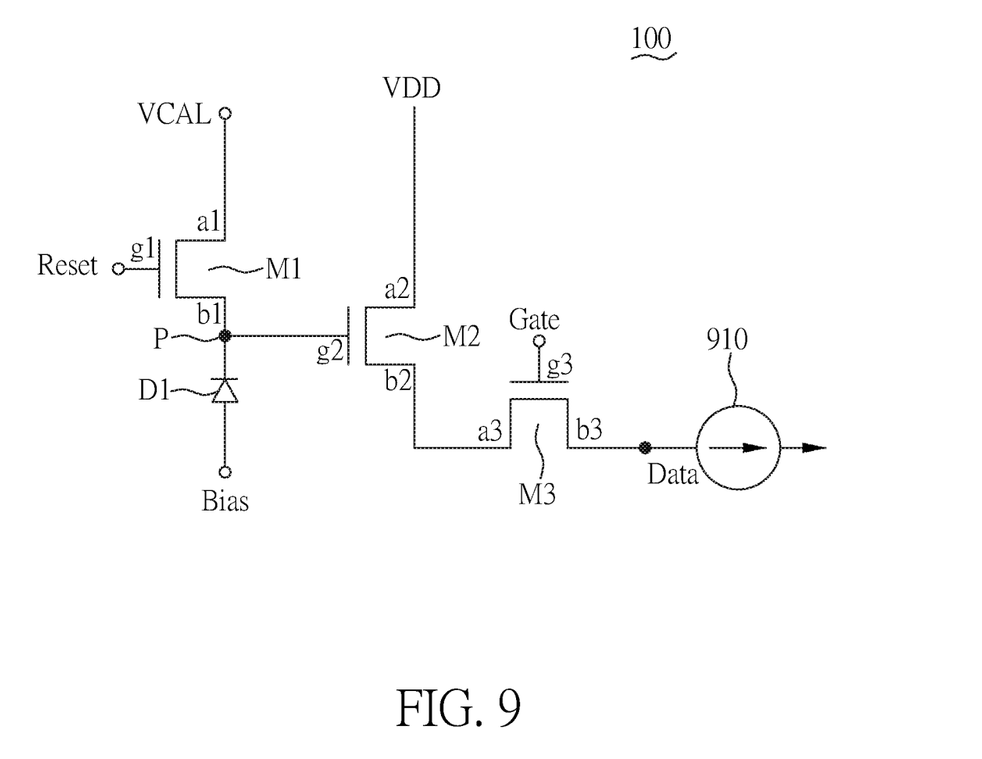
FIG. 9 is a circuit diagram of an embodiment of the pixel circuit of an X-ray sensor according to the present disclosure.

FIG. 9 is a circuit diagram of an embodiment of the pixel circuit 100 of an X-ray sensor according to the present disclosure, which is similar to FIG. 3 except that FIG. 9 further includes a constant current source 910. The constant current source 910 is electrically connected with the second terminal b3 of the third transistor M3, thereby allowing the second transistor M2 to be operated in a source follower mode to measure the voltage change of the node Data when being exposed to the X-ray. In this embodiment, the operation in the source follower mode reduces the influence on the voltage measurement, induced by the manufacturing variation of the components (such as the second transistor M2 or the photo diode D1).

Figure 10:
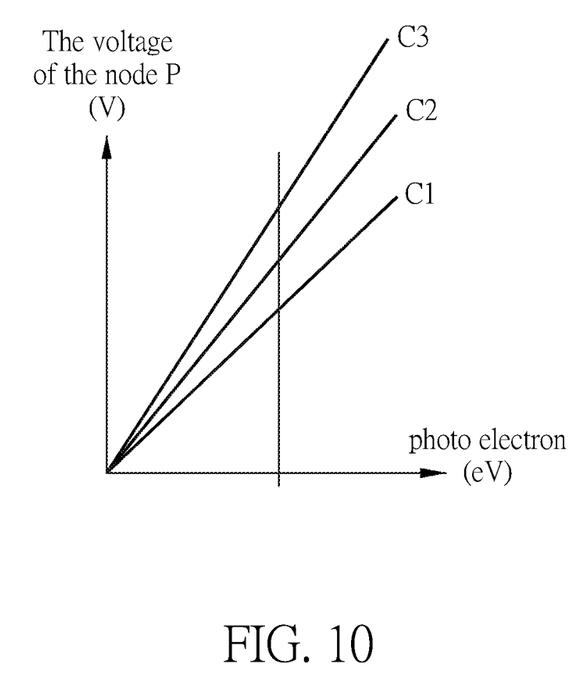
FIG. 10 is a voltage diagram for node P in the pixel circuit of an X-ray sensor according to the present disclosure.

FIG. 10 is a voltage diagram for the node P in the pixel circuit 100 of an X-ray sensor according to the present disclosure. The photo diode can generate the same amount of photo electrons when being exposed to the same X-ray. As shown in FIG. 10, the photo electrons on the horizontal axis is represented with unit of electron voltage (eV), and the voltage of the node P on the vertical axis is represented with a unit of volt (V). However, since the manufacturing process causes each photo diode to have a different capacitance, each node P has a different voltage as well. The readout circuit can read out the electrical signal from the second terminal b3 of the third transistor M3 to obtain the voltages of the node P corresponding to the different photo diodes. In other cases, it is possible to apply an electrical signal to the photo diode to simulate the exposure to the X-ray.

Figure 11:
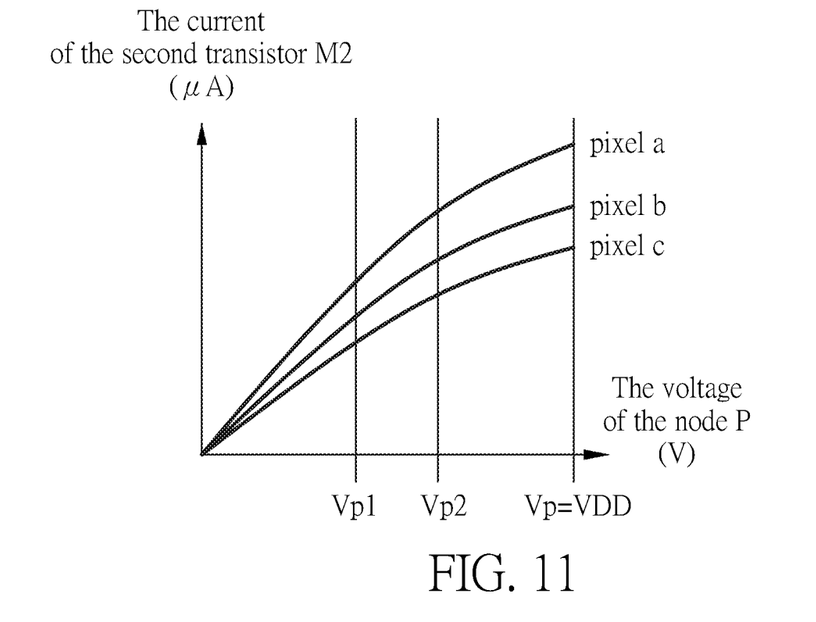
FIG. 11 is a current diagram for the second transistor in the pixel circuit of an X-ray sensor according to the present disclosure.

FIG. 11 is a current diagram for the second transistor M2 in the pixel. circuit 100 of the X-ray sensor according to the present disclosure. As shown in FIG. 11, the voltage of the node P on the horizontal axis is represented with unit of volt (V), and the current of the second transistor M2 on the vertical axis is represent with unit of micro amp (μA). From the pixel a to the pixel c, since the second transistors M2 in different pixel circuits 100 may have threshold voltages Vth with certain variation caused by the manufacturing process, the second transistors M2 corresponding to different pixels may generate different currents even if the nodes P are applied with the same voltage.

Figure 12:
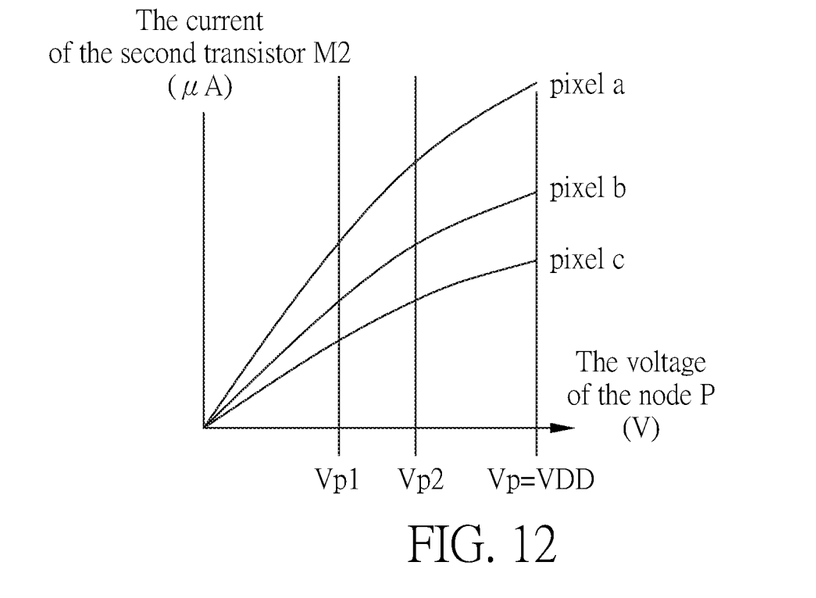
FIG. 12 is another current diagram for the second transistor in the pixel circuit of an X-ray sensor according to the present disclosure.

FIG. 12 is another current diagram for the second transistor M2 in the pixel circuit 100 of the X-ray sensor according to the present disclosure. In other words, FIG. 12 is a current diagram for the current change of the second transistor M2 with respect to the voltage change of node P when the X-ray sensor is exposed to different X-rays. As shown in FIG. 12, the voltage of the node P on the horizontal axis is represented with unit of volt (V), and the current of the second transistor M2 on the vertical axis is represented with unit of micro amp (μA). From the pixel a to the pixel c, since, in different pixel circuits 100, the photo diodes may have capacitance variation and the second transistors M2 may have threshold voltage shift (Vth shift), caused by the manufacturing process, the pixel circuits 100 corresponding to different pixels may generate different currents even if being inputted with the same amount of X-ray. However, by using the circuits in FIG. 3 to FIG. 9 according to the present disclosure, it is possible to perform compensation to the threshold voltage shift (Vth shift) of the second transistor M2 or to the capacitance variation of the photo diode, and thus reduce the difference of the currents outputted from the pixel circuits 100 of the pixel a to the pixel c, thereby improving the accuracy of imaging provided by the pixel circuit 100 of the X-ray sensor.

Figure 13:
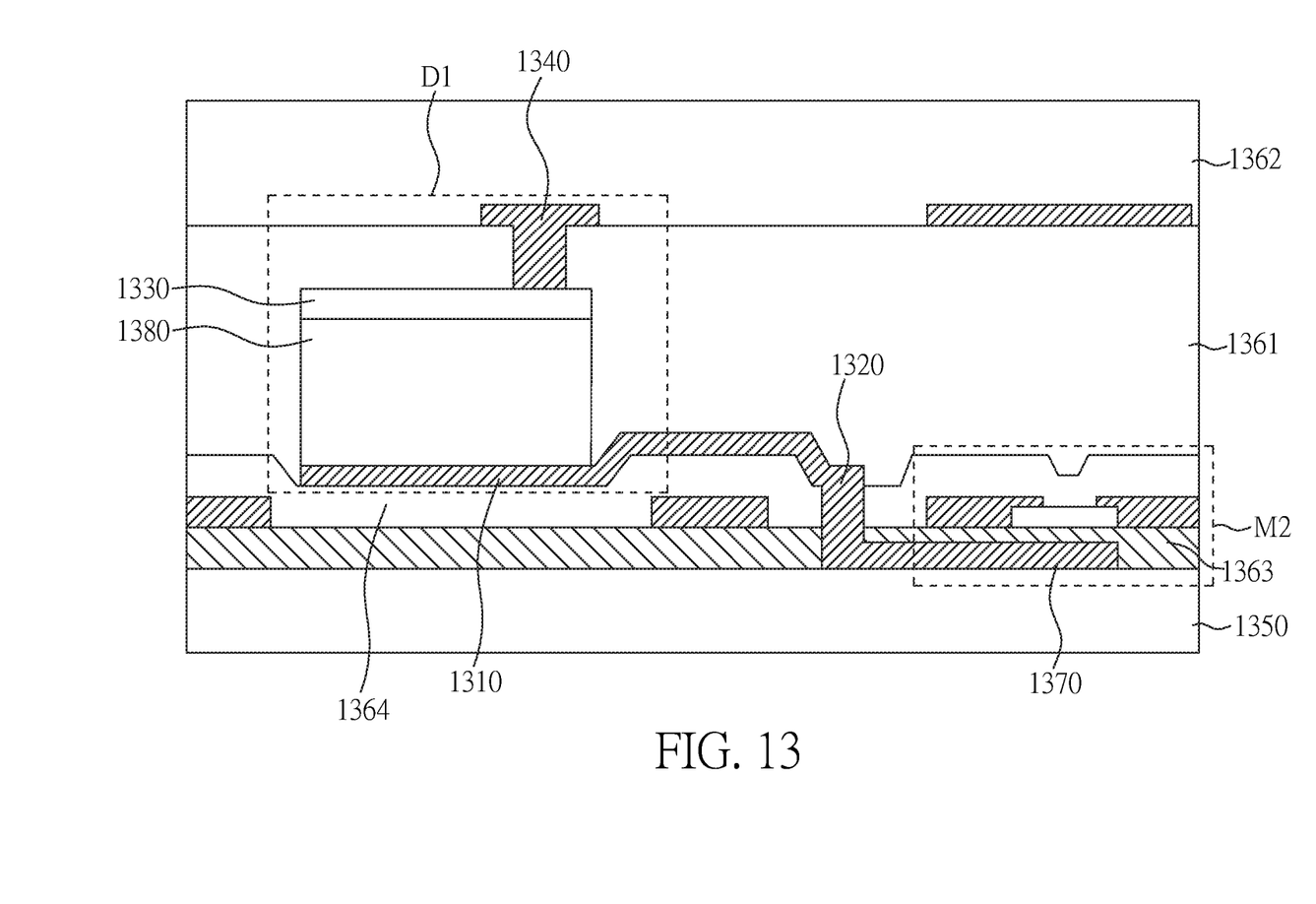
FIG. 13 is a stack diagram of the second transistor and the photo diode according to the present disclosure.

FIG. 13 is a stack diagram of second transistor M2 and photo diode D1 according to the present disclosure. As shown, a gate 1370 of the second transistor M2 is disposed on a substrate 1350, and a dielectric layer 1363 is further disposed on the gate 1370. An active layer, a drain and a source of the second transistor M2 are disposed on the dielectric layer 1363, and they form the second transistor M2 in combination of the gate 1370. A dielectric layer 1364 is disposed on the active layer, the drain and the source of the second transistor M2. A bottom electrode 1310 of the photo diode D1 is disposed on the dielectric layer 1364. The bottom electrode 1310 can be electrically connected with the gate 1370 of the second transistor M2 by a tracing wire 1320 through via holes of the dielectric layer 1364 and the dielectric layer 1363. A sensing region 1380 is disposed on a part of the bottom electrode 1310. A top electrode 1330 is disposed on the sensing region 1380. A dielectric layer 1361 is disposed on a part of the dielectric layer 1364, a part of the tracing wire 1320, a part of the bottom electrode 1310, and the top electrode 1330. A bias electrode 1340 can be electrically connected with the top electrode 1330 of the photo diode D1 through a via hole of the dielectric layer 1361, wherein the top electrode 1330 of the photo diode D1 is made of material of, for example, indium tin oxide (ITO). In this embodiment, since the dielectric layer 1364 is, for example, uniformly disposed on the second transistor M2 and other transistors or wires, the surface of the dielectric layer 1364 may be uneven with respect to the components covered by it, and the bottom electrode 1310 disposed on the dielectric layer 1364 may be also uneven with respect to the dielectric layer 1364. Hence, when the sensing region 1380 of the photo diode D1 is being disposed on the bottom electrode 1310, it is advised to avoid the regions (for example, the regions on the second transistor M2 or other components) with uneven surface, but to choose a flat region (for example, the region as shown in FIG. 13) for the arrangement.

Figure 14:
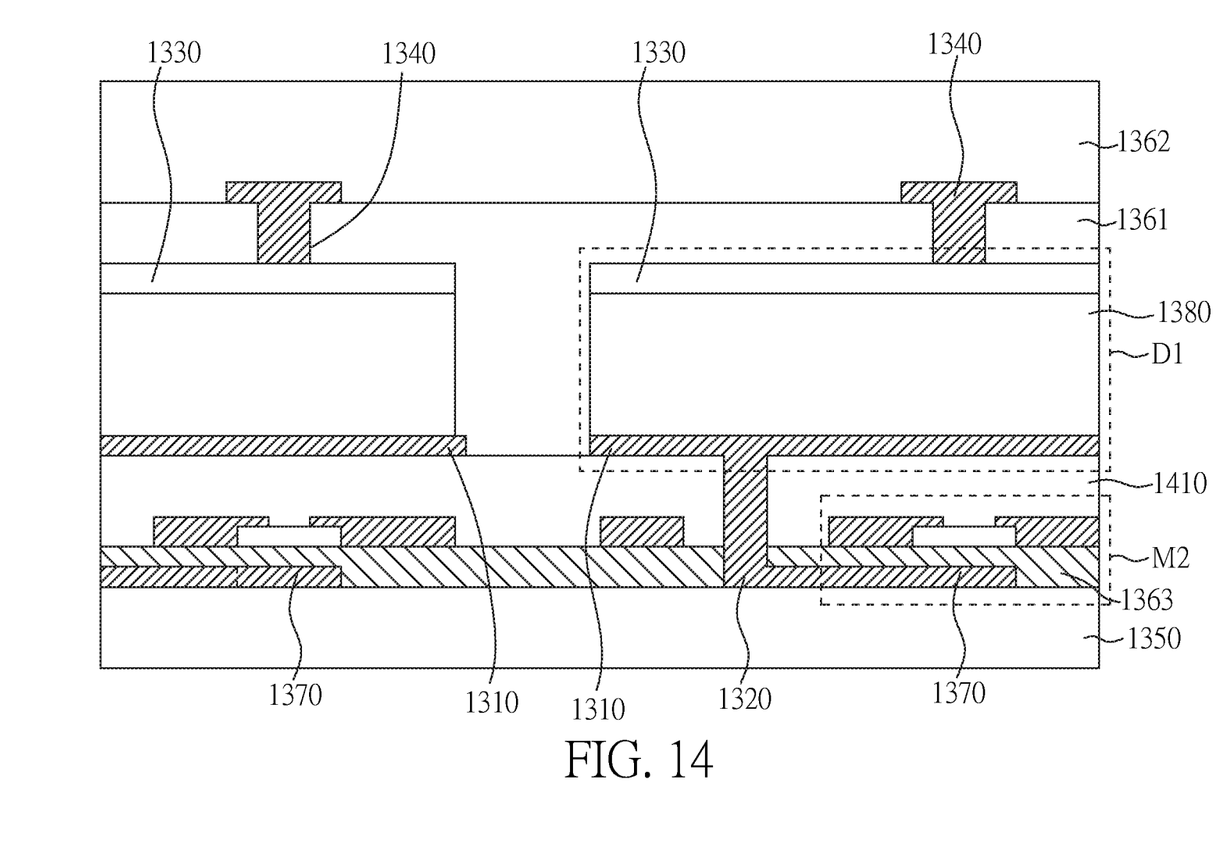
FIG. 14 is another stack diagram of the second transistor and the photo diode according to the present disclosure.

FIG. 14 is another stack diagram of the second transistor M2 and the photo diode D1 according to the present disclosure. As shown, a flat layer 1410 is disposed below the bottom electrode 1310 of the photo diode D1, and the flat layer 1410 is made of dielectric materials, so that the photo diode D1 can be disposed adjacent to the second transistor M2 or on the second transistor M2. In this case, at a least a portion of the photo diode overlaps the second transistor. This reduces the circuit layout area.

Figure 15:
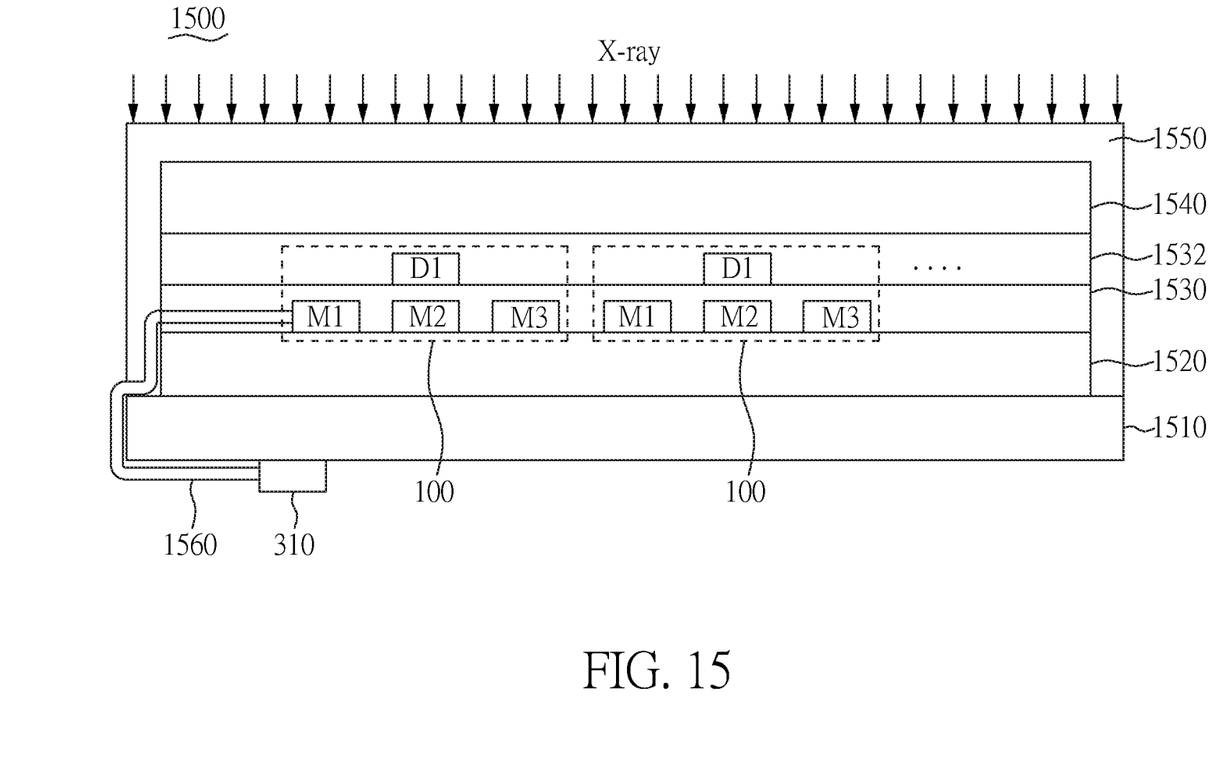
FIG. 15 is a stack diagram of the X-ray sensor according to the present disclosure.

FIG. 15 is a stack diagram of the X-ray sensor 1500 according to the present disclosure. As shown, the X-ray sensor 1500 includes a carrier 1510, a substrate 1520, a plurality of pixel circuits 100, a flat layer 1530, a dielectric layer 1532, a scintillator layer 1540 and a protective layer 1550.

As shown in FIG. 15, the substrate 1520 can be disposed on the carrier 1510. A plurality of first transistors M1, a plurality of second transistors M2 and a plurality of third transistors M3 are disposed on the substrate 1520. The flat layer 1530 is disposed on the first transistors M1, the second transistors M2 and the third transistors M3. A plurality of photo diodes D1 are disposed on the flat layer 1530. The dielectric layer 1532 is disposed on the photo diodes D1 and a part of the flat layer 1530. The scintillator layer 1540 is disposed on the dielectric layer 1532. A programmable voltage source 310 or other components, such as a digital-to-analog converting circuit or a control unit, can be disposed on another side of the carrier 1510 opposite to the substrate 1520, and electrically connected with the pixel circuit 100 through a flexible cable 1560. In other embodiments, the programmable voltage source 310 or the other components, such as the digital-to-analog converting circuit or the control unit, can also be disposed on the carrier 1510 or on the substrate 1520, and electrically connected with the pixel circuit 100 through the flexible cable 1560. Alternatively, they can be disposed on the side surface of the carrier 1510 or on the side surface of the substrate 1520, and electrically connected with the pixel circuit 100 through the flexible cable 1560. However, the present disclosure is not limited to the aforementioned structures. The protective layer 1550 can be disposed, for example, on the top surface of the scintillator layer 1540 or the side surface thereof, on the side surface of the dielectric layer 1532, on the side surface of the flat layer 1530, on the side surface of the substrate 1520 or on a part of the top surface of the carrier 1510. Finally, the structure of the X-ray sensor 1500 in FIG. 15 can be received in a housing (not shown), wherein the material of the housing in the incident surface (or region) of the X-ray is chosen to be, for example, carbon fiber, that allows the X-ray to pass through, while the material of the housing in other surface (or region) is chosen to be, for example, metal, that can support and protect the X-ray sensor 1500. Each pixel circuit 100 includes a photo diode D1, a first transistor M1, a second transistor M2 and a third transistor M3. The pixel circuits 100 are disposed on the substrate 1520 as a matrix. The photo diode D1 of each pixel circuit 100 can be used to sense X-rays and to generate a corresponding electrical sensing signal. The first transistor M1 of each pixel circuit 100 can be electrically connected with the photo diode D1 of the pixel circuit 100 to reset the electrical sensing signal. In this embodiment, the scintillator layer 1540 is disposed on the whole layer, while, in other embodiments, the scintillator layer 1540 can be patterned and disposed corresponding to the pixel region. In this embodiment, the scintillator layer 1540 is formed of materials such as caesium iodide (CsI) or gadolinium oxysulfate (Gd2O2S), and the protective layer 1550 is formed of materials such as aluminum or polyimide (PI), but the present disclosure is not limited to the aforementioned materials.

With reference to FIG. 1, a terminal of the first transistor M1 is electrically connected with the calibration voltage VCAL. The second transistor M2 of each pixel circuit 100 can be electrically connected with the photo diode D1 and the first transistor M1 of the pixel circuit 100. The second transistor M2 can be used to amplify the electrical sensing signal and to generate an amplified sensing signal, wherein a terminal a2 of the second transistor M2 is electrically connected with a high voltage VDD. The third transistor M3 of each pixel circuit 100 is electrically connected with the second transistor M2 of the pixel circuit 100 to output the amplified sensing signal to the readout circuit.

The photo diode D1 of the pixel circuit 100 is disposed on the second transistor M2 through the flat layer 1530, and this reduces the circuit layout area.

The scintillator layer 1540 is disposed on the photo diodes D1, the first transistors M1, the second transistors M2 and third transistors M3 of a plurality of pixel circuits 100 to convert the X-ray into a visible light, thereby allowing the photo diode D1 to generate the corresponding electrical sensing signal. The protective layer 1550 can be disposed on the scintillator layer 1540 to prevent the scintillator layer 1540 from being damaged by impurities such as steam or dust.

As previously explained, in the embodiment of the present disclosure, the high voltage VDD and the calibration voltage VCAL are electrically connected with the second transistor M2 and the first transistor M1 through different wires, respectively. Therefore, the high voltage VDD and the calibration voltage VCAL can be controlled separately, and thus the high voltage VDD can be the same as or different from the calibration voltage VCAL. In the present disclosure, a variable calibration voltage VCAL is provided to a terminal of the first transistor M1, so that it is possible to measure and compensate the threshold voltage shift of the second transistor M2, or the capacitance variation of the photo diode D1, and thus reduce the difference of the currents outputted from the pixel circuits, thereby improving the accuracy of imaging provided by the pixel circuit 100 of the X-ray sensor.

Even if the present disclosure has been explained in relation to the aforementioned embodiment, it is to be understood that many other possible modifications and variations can be made without departing from the spirit and scope of the claims.

What is claimed is:

1. A pixel circuit of an Xray sensor, comprising:
    a photo diode used to sense X-rays and to generate a corresponding electrical sensing signal;
    a first transistor electrically connected with the photo diode to reset the electrical sensing signal;
    a second transistor electrically connected with the photo diode and the first transistor to amplify the electrical sensing signal and to generate an amplified sensing signal; and
    a third transistor electrically connected with the second transistor o output the amplified sensing signal,
    wherein the second transistor has a terminal electrically connected with a high voltage, the first transistor has a terminal electrically connected with a calibration voltage, and the high voltage and the calibration voltage are controlled separately.

2. The pixel circuit of the X-ray sensor as claimed in claim 1, wherein the calibration voltage is variable.

3. The pixel circuit of the X-ray sensor as claimed in claim 1, wherein the first transistor has a control terminal electrically connected with a first control signal, a first terminal electrically connected with the calibration voltage, and a second terminal electrically connected with the photo diode; the second transistor has a control terminal electrically connected with the photo diode, and a first terminal electrically connected with the high voltage; the third transistor has a control terminal electrically connected with a second control signal, and a first terminal electrically connected with the second terminal of the second transistor.

4. The pixel circuit of the X-ray sensor as claimed in claim 1, further comprising:
    a programmable voltage source electrically connected with the first transistor to provide the calibration voltage.

5. The pixel circuit of the X-ray sensor as claimed in claim 1, further comprising:
    a digital-to-analog converting circuit electrically connected with the first transistor; and
    a control unit electrically connected with the digital-to-analog converting circuit to control the digital-to-analog converting circuit to generate the calibration voltage.

6. The pixel circuit of the X-ray sensor as claimed in claim 1, further comprising:
    an N-to-1 switch electrically connected with the first transistor, wherein the N-to-1 switch has N input terminals electrically connected with N different voltages, and the N-to-1 switch has an output terminal electrically connected with the first transistor to provide the calibration voltage, where N is an positive integer greater than 1.

7. The pixel circuit of the X-ray sensor as claimed in claim 1, further comprising:
   a switch electrically connected with the first transistor;
   a programmable voltage source electrically connected with the switch to provide the calibration voltage;
   a readout circuit electrically connected with the switch to perform integral operation on the electrical sensing signal; and
   an analog-to-digital converting circuit electrically connected with the readout circuit.

8. The pixel circuit of the X-ray sensor as claimed in claim 7, wherein the readout circuit further comprises an operational amplifier and a capacitor.

9. The pixel circuit of the X-ray sensor as claimed in claim 8, wherein the operational amplifier has an inverting terminal electrically connected with a first terminal of the switch, and a non-inverting terminal electrically connected with a reference voltage.

10. The pixel circuit of the X-ray sensor as claimed in claim 9, wherein the capacitor has one terminal electrically connected with the inverting terminal, and another terminal electrically connected with an output terminal of the operational amplifier.

11. The pixel circuit of the X-ray sensor as claimed in claim 10, wherein the analog-to-digital converting circuit is electrically connected with the output terminal of the operational amplifier.

12. The pixel circuit of the X-ray sensor as claimed in claim 1, further comprising:
   a digital-to-analog converting circuit electrically connected with the photo diode; and
   a control unit electrically connected with the digital-to-analog converting circuit to control the digital-to-analog converting circuit to generate a photo diode calibration voltage.

13. The pixel circuit of the X-ray sensor as claimed in claim 1, wherein the photo diode is disposed adjacent to the second transistor.

14. The pixel circuit of the X-ray sensor as claimed in claim 1, wherein the photo diode disposed on the second transistor and at a least a portion of the photo diode overlaps the second transistor.

15. An X-ray sensor, comprising:
   a carrier;
   a substrate disposed on the carrier;
   a pixel circuit disposed on the substrate, the pixel circuit comprising:
      a photo diode used to sense X-rays and to generate a corresponding electrical sensing signal;
      a first transistor electrically connected with the photo diode to reset the electrical sensing signal, wherein the first transistor has a terminal electrically connected with a calibration voltage;
      a second transistor electrically connected with the photo diode and the first transistor to amplify the electrical sensing signal, and to generate an amplified sensing signal, wherein the second transistor has a terminal electrically connected with a high voltage, and the high voltage and the calibration voltage are controlled separately; and
      a third transistor electrically connected with the second transistor to output the amplified sensing signal;
   a scintillator layer disposed on the pixel circuit to convert the X-ray into a visible light, allowing the photo diode to generate the corresponding electrical sensing signal; and
   a protective layer disposed on the scintillator layer.

16. The X-ray sensor as claimed in claim 15, wherein the photo diode is disposed adjacent to the second transistor.

17. The X-ray sensor as claimed in claim 15, wherein the photo diode disposed on the second transistor and at a least a portion of the photo diode overlaps the second transistor.

18. The X-ray sensor as claimed in claim 15, wherein the first transistor has a control terminal electrically connected with a first control signal, a first terminal electrically connected with the calibration voltage, and a second terminal electrically connected with the photo diode; the second transistor has a control terminal electrically connected with the photo diode, and a first terminal electrically connected with the high voltage; the third transistor has a control terminal electrically connected with a second control signal, and a first terminal electrically connected with the second terminal of the second transistor.

19. The X-ray sensor as claimed in claim 15, further comprising:
   a programmable voltage source electrically connected with the first transistor to provide the calibration voltage.

20. The X-ray sensor as claimed in claim 15, further comprising:
   a digital-to-analog converting circuit electrically connected with the first transistor; and
   a control unit electrically connected with the digital-to-analog converting circuit to control the digital-to-analog converting circuit to generate the calibration voltage.

* * * * *